United States Patent

Purwar et al.

[11] Patent Number: 5,843,930
[45] Date of Patent: Dec. 1, 1998

[54] METHOD OF TREATING OTITIS WITH CIPROFLOXACIN-HYDROCORTISONE SUSPENSION

[75] Inventors: Shivaji Purwar, Monroe; David Goldman, Easton, both of Conn.

[73] Assignee: Bayer Corporation, Pittsburgh, Pa.

[21] Appl. No.: 838,473

[22] Filed: Apr. 7, 1997

Related U.S. Application Data

[60] Continuation-in-part of Ser. No. 709,245, Jul. 23, 1996, abandoned, which is a division of Ser. No. 465,048, Jun. 6, 1995, abandoned.

[51] Int. Cl.⁶ .......................... A61K 31/495; A61K 31/56
[52] U.S. Cl. ........................... 514/171; 514/254; 424/437
[58] Field of Search .................... 514/254, 171; 424/437

[56] References Cited

U.S. PATENT DOCUMENTS

| | | | |
|---|---|---|---|
| 4,025,620 | 5/1977 | Beyer et al. | 424/115 |
| 4,670,444 | 6/1987 | Grohe | 514/300 |
| 4,844,902 | 7/1989 | Grohe | 424/449 |
| 4,957,922 | 9/1990 | Lammens et al. | 514/255 |
| 5,023,257 | 6/1991 | Pöllinger et al. | 514/254 |
| 5,061,729 | 10/1991 | Kincses et al. | 514/562 |
| 5,063,061 | 11/1991 | Yazaki et al. | 424/427 |
| 5,260,073 | 11/1993 | Phipps | 424/465 |
| 5,271,939 | 12/1993 | Robertson et al. | 424/427 |
| 5,422,116 | 6/1995 | Yen et al. | 424/427 |
| 5,580,575 | 12/1996 | Unger et al. | 424/450 |

FOREIGN PATENT DOCUMENTS

| | | | |
|---|---|---|---|
| 0689832 | 1/1996 | European Pat. Off. | A61K 9/08 |

OTHER PUBLICATIONS

Strauss, M., et al., Otitis External Associated With Aquatic Activities (Swimmer's Ear), Clinics in Dermatology, 1987, pp. 103–111.

Stange, G., et al., Laryngol Rhino Otol 68 (12) : 653–656 (1989) [Abstract].

Stange, G., et al., Laryngol Rhino Otol 68 (12) : 653–656 (1989), Abstract.

Esposito, S., et al., Topical and Oral Treatment of Chronic Otitis Media With Ciprofloxacin, Arch Otolaryngol Head Neck Surg — vol. 116, 1990, pp. 557–559.

García–Rodriguez, J.A., et al., Efficacy of 2 Regimens of Local Ciprofloxacin in the Treatment of Ear Infections, Preprint: Drugs 45 (Suppl.), 1993, pp. 40–41.

Ganz, H., Bacterial Otitis Externa Beyond the Organ Limits — Systemic and Topical Combination Treatment with Ciprofloxacin, pp. 2–7 (translation from German) 1992.

García–Rodriguez, J.A., Efficacy of Topical Ciprofloxacin in the Treatment of Ear Infections in Adults, J Antimicrob Chemother, 1993, pp. 31:452–453.

Esposito, S., et al., Topical Cirpofloxacin (CP) Versus Parenteral Gentamicin (GM) in Pseudomonas Infections of the Middle Ear, 29. Interscience Conference Antimicrobiotic Agents Chemotherapy +* Houston, 545 (1989) [Abstract].

*Primary Examiner*—Rebecca Cook

[57] ABSTRACT

The invention is directed to a method of treating otitis which comprises introducing an antibacterially-effective amount of a composition comprising a non-ototoxic, topical, otic pharmaceutic composition comprising (a) ciprofloxacin in aqueous solution in an amount effective for antibacterial action; (b) a non-ionic viscosity augmenter unaffected by pH and ionic level, said viscosity augmenter being present in an amount effective for augmenting viscosity of the composition to a viscosity greater than that of water, said viscosity augmenter being at least 85% hydrolyzed polyvinyl alcohol; (c) a non-ototoxic preservative present in an amount effective for antibacterial action, the preservative being benzyl alcohol; (d) water sufficient to produce an aqueous composition; (e) hydrocortisone in aqueous suspension in an amount effective for anti-inflammatory action; (f) lecithin in an amount effective for enhancing suspension of other constituents in the composition; and (g) polysorbate ranging from polysorbate 20 to 80 in an amount effective for spreading the preparation on a hydrophobic skin surface to the site of infection or inflammation.

1 Claim, No Drawings

METHOD OF TREATING OTITIS WITH CIPROFLOXACIN-HYDROCORTISONE SUSPENSION

This application is a continuation-in-part of application Ser. No. 08/709,245 filed on Jul. 23, 1996, abandoned which is a divisional of U.S. application Ser. No. 08/465,048 filed Jun. 6, 1995 abandoned.

FIELD

This invention relates to compositions and methods for treating otitis externa (external ear infections) and otitis media (middle ear infections) specifically otorrhea (otitis media with ruptured ear drum causing effusion).

BACKGROUND

Otitis external involving the ear canal portion of the external ear, is a common otologic problem occurring mainly during hot, humid weather, and five times more frequently in swimmers than in nonswimmers. In the incipient stage, symptoms include itching and pain in the ear canal, and tenderness when pressure is applied around the external auditory meatus, the ear lobe is pulled or the jaw is moved. In the definitive stage, suppuration occurs in the ear canal and hearing may be decreased. Over 90% of cases of otitis externa are due to bacterial and fungal infections. Treatment with topical agents is common, including antibacterial and/or antifungal creams and drops. Oral antibiotics may be used if cellulitis symptoms are present.

Otitis media, a term used to describe infections of the middle ear, is also very common. A relatively high percentage of the population, both adults and particularly children, are affected. It has been estimated that nearly 95% of all children experience one or more episodes of otitis by age 9, and that about 15% of all visits by children to pediatricians are in regard to otitis media. In children, the diseases is most often associated with upper respiratory afflictions which trigger a transudate secretion response in the Eustachian tube and middle ear. Bacteria and viruses migrate from the naso-pharynx to the middle ear via the Eustachian tube, and can cause the Eustachian tube to become blocked, preventing ventilation and drainage of the middle ear.

In its more severe forms, purulent exudate, toxins and endogenous anti-microbial enzymes are formed in the middle ear, which can cause irreparable damage to sensory-neural and sound conducting structures. It has been reported that sensory-neural hearing loss occurred in 35.8 percent of children with otitis media with effusion. It is estimated that over one billion dollars are spent annually in the United States on the treatment and prevention of otitis media.

Current methods of treatment generally involve the systemic use of antibiotics; the use of ear drops (which have not been approved by the Food and Drug Administration); and in more chronic cases, the insertion of a myringotomy tube through an incision in the eardrum to allow ventilation and drainage of the middle ear cavity. Systemic administration of antibiotics generally requires high initial doses and an appreciable time lag to achieve therapeutic levels in the middle ear. With respect to currently known ear drops, there has been growing concern recently that medications in the middle ear cavity as well as inflammatory and infectious substances can cause inner ear damage. It is generally believed that damaging substances in the middle ear space can gain access into the inner ear across the round window membrane, which has been demonstrated to be semipermeable. Hearing loss is believed a result of impairment, damage or destruction of inner ear cochlear hair cells.

Ciprofloxacin and its preparation is described in U.S. Pat. No. 4,670,444, which is hereby incorporated by reference. Studies have shown the usefulness of local ciprofloxacin in ear infections. A study of the clinical and bacteriological efficacy of ciprofloxacin in human patients affected by chronic otitis media in the acute stage is reported in "Topical and Oral Treatment of Chronic Otitis Media With Ciprofloxacin" by Esposito, D'Errico and Montanaro in *Arch. Otolaryngo Head Neck Surg.*, Vol 116, May 1990, p.556–559. Three drops of ciprofloxacin in saline solution were administered twice a day in affected ears for 5 to 10 days. A high percentage of favorable clinical response and bacteriological eradication was observed without ototoxicity.

A study entitled "Local Therapy for Pseudomonas Infections of the Ear" by G. Stang in *Laryngol Rhino Otol.* 68 (12): 653–656 (1989) reports that infections of the middle and external ear in humans caused by *Pseudononas aeruginosa* can be cured by local therapy with ciprofloxacin and tutofusin very quickly and without any complications. Function disturbance of the middle and internal ear cleared up and the functions returned to normal.

A study of the "Efficacy of 2 Regimens of Local Ciprofloxacin in the Treatment of Ear Infections" by Garcia-Rodriguez et al was reported in *Preprint: Drugs* 45 (Suppl.) 1993, pages 40–41. Ear infections of several types were treated with 3 drops per 8 hours for 7 days with 0.5% ciprofloxacin solution and in another group of patients with 0.3% ciprofloxacin solution. The results obtained showed that local ciprofloxacin is an effective treatment for ear infections with few and mild side effects and without ototoxicity.

While ciprofloxacin-containing ear drops have been prepared and administered in studies, currently, there is no ciprofloxacin or other antibiotic preparation approved for topical middle ear use, and which can be prescribed for a patient. What is needed is a non-irritating, non-sensitizing, non-ototoxic composition which can be readily used by a patient for topical treatment of otitis, particularly otitis media, and most particularly, otorrhea.

SUMMARY

This invention provides a non-ototoxic, non-irritating and non-sensitizing composition for introduction, preferably by instillation, into human and animal ears for the treatment of otitis externa and otitis media, particularly otorrhea. The composition will reach the middle ear through a ruptured ear drum to the site of infection, spread over an infected area, and deposit in a sufficient layer to provide an anti-bacterial effect. The composition comprises ciprofloxacin in an amount effective for antibacterial action; a non-ionic viscosity augmenter unaffected by pH and ionic level in an amount effective for augmenting viscosity of the composition to a viscosity greater than that of water; and water sufficient to produce a liquid composition. The viscosity augmenter is chosen from the group consisting of methylcellulose, polyvinyl alcohol, and glycerine.

One embodiment provides a composition in which all constituents are in solution. The composition comprises: ciprofloxacin in an amount effective for anti-bacterial action; methylcellulose in an amount effective for augmenting the viscosity of the composition to a viscosity greater than that of water; potassium sorbate in an amount effective as a preservative against contamination by microorganisms; sodium acetate and acetic acid in effective amounts for buffering the composition to a pH in a range from about 3 to about 6; a polysorbate ranging from polysorbate 20 to 80 in an effective amount for spreading the composition on a hydrophobic skin surface; and water sufficient to produce a liquid composition.

Another effective composition provided by this embodiment is the latter further comprising glycerin in an effective amount to adjust the tonicity of the composition from about 200 to about 600 milliosmoles, that is, to provide a composition which is approximately isotonic.

Another embodiment provides ciprofloxacin-containing aqueous compositions including an anti-inflammatory agent, preferably hydrocortisone. Hydrocortisone being insoluble in water, the composition is a suspension thereof and comprises: ciprofloxacin in an amount effective for anti-bacterial action; hydrocortisone in an amount effective for anti-inflammatory action; polyvinyl alcohol in an amount effective for augmenting viscosity of the composition to a viscosity greater than that of water and suspending other constituents; lecithin in an amount effective for enhancing suspension of other constituents; benzyl alcohol in an amount effective as a preservative against contamination by microorganisms; sodium acetate and acetic acid in effective amounts for buffering the composition to a pH in the range from about 3 to about 6; a polysorbate ranging from polysorbate 20 to 80 in an effective amount for spreading the composition on a hydrophobic skin surface; and water sufficient to produce a liquid composition.

Another effective suspension composition is the latter further comprising sodium chloride in an effective amount to adjust the tonicity of the composition from about 200 to about 600 milliosmoles, that is, to render the composition approximately isotonic.

In the compositions including hydrocortisone, each of the other constituents enhance or do not impair the resuspendability of the insoluble constituent hydrocortisone. Therefore a high degree of suspension stability and uniformity is achieved whereby the compositions are stable over long shelf life and are convenient and acceptable to users for topical treatment of conditions such as otitis.

Yet another embodiment provides a composition wherein glycerine augments the viscosity of the aqueous solution to a viscosity greater than that of water. The composition comprises: ciprofloxacin in an amount effective for anti-bacterial action; glycerine in an amount effective for augmenting the viscosity of the composition to a viscosity greater than that of water; and water sufficient to produce a liquid composition.

The invention also provides a method of treating otitis which comprises introducing an anti-bacterially effective amount of a composition as described above topically to the site of infection or inflammation. A preferred method is instilling the composition into the ear. If the ear drum is perforated, the composition can penetrate to the middle ear. Otherwise the composition can be introduced into the middle ear, for example, through a myrogotomy tube, or through the Eustachian tube by the method described in German Patent No. DE 3,617,400. To some degree, the composition can also diffuse into adjoining tissues and the middle ear when an intact ear drum is present.

Effective amounts of composition for introduction into the ear are preferably one to five drops twice daily, that is, from about 40 to about 200 µl per application.

DESCRIPTION

According to this invention, water, being not ototoxic, irritating or sensitizing in the ear, is the base for a solution composition containing ciprofloxacin, which is highly anti-bacterial in otitis treatment. Amounts of ciprofloxacin in aqueous solution effective for anti-bacterial action range from about 0.01 to about 1 weight percent, preferably from about 0.1 to about 0.5 weight percent, most preferably about 0.2 weight percent.

To prevent contamination by microorganisms and provide a reasonable shelf life, the Otic composition provided by this invention includes a preservative. The required properties for a preservative compatible with ciprofloxacin were met with difficulty. Acceptable preservatives were required to cause no or insignificant ototoxicity, sensitization or irritation of the ear. Another requirement was that the preservative be jointly soluble with ciprofloxacin in water over a common pH range inasmuch as ciprofloxacin solubility was limited to pH's less than about 6. In aqueous solutions containing from about 0.2 to about 1 weight percent of ciprofloxacin hydrochloride, crystalline precipitation was observed to occur at pH's above 5.5 at room temperature, and at pH's above 5 at 5 C.

Potassium sorbate, sodium benzoate and benzyl alcohol were candidate preservatives. In aqueous solutions at 5 C containing from about 0.2 to 0.3 weight percent sodium benzoate, precipitation of crystals was observed at pH's lower than about 4.5 to 5. In aqueous solutions at 5 C containing from about 0.1 to 0.15 weight percent potassium sorbate, precipitation of crystals was observed at pH's lower than 4.5. In view of the experimentally determined pH ranges for aqueous solubility of ciprofloxacin hydrochloride and potassium sorbate, aqueous solutions containing these materials preferably have a pH range of about 3 to about 6, most preferably, about 4.75.

Potassium sorbate in concentrations of 0.13, 0.104 and 0.065 weight percent; sodium benzoate in a concentration of 0.24 weight percent; and benzyl alcohol at concentrations of 0.9, 0.72 and 0.45 weight percent were found to be effective preservatives in aqueous ciprofloxacin hydrochloride solutions in preservative challenge tests conducted pursuant to the procedure described in the United States Pharmacopeia, Edition XXIII, 1995, page 1681, hereby incorporated by reference. Amounts of potassium sorbate effective as a preservative for ciprofloxacin hydrochloride in aqueous solution range from about 0.01 to about 1 weight percent, preferably from about 0.05 to about 0.5 weight percent, and most preferably about 0.13 weight percent. Amounts of benzyl alcohol effective as a preservative in aqueous preparations with ciprofloxacin hydrochloride range from about 0.1 to about 3 weight percent, preferably from about 0.1 to about 2 weight percent, and most preferably about 0.9 weight percent. The solubility of ciprofloxacin hydrochloride being unaffected by benzyl alcohol, solutions of these materials may have a pH below about 6, and preferably about 4.75.

Because the aqueous solubilities of ciprofloxacin hydrochloride and potassium sorbate are limited to a narrow mutual pH range, a buffering agent is desirable when potassium sorbate is used as a preservative in ciprofloxacin hydrochloride solutions. Citrate buffer caused precipitation of ciprofloxacin and was unsuitable. Acetate buffer was found effective at a concentration of 0.05 molar. Amounts of sodium acetate and acetic acid effective to buffer the preparation range from about 0.1 to about 3 weight percent of sodium acetate and from about 0.01 to about 10 weight percent of acetic acid; preferably from about 0.1 to about 2 weight percent of sodium acetate and from about 0.1 to about 5 weight percent of acetic acid; and most preferably about 0.4 weight percent of sodium acetate and about 0.7 weight percent of acetic acid.

Benzyl alcohol having a solubility in aqueous solutions independent of pH, and ciprofloxacin hydrochloride having solubility in aqueous solutions at pH less than about 6, solutions including these components do not need to be buffered, but may be simply adjusted with hydrochloric acid or sodium hydrochloride to a pH less than about 6, preferably to a pH of about 4.75. A buffer, however, such as an acetate buffer, may be included.

To allow the ciprofloxacin liquid preparation to be administered in drops from a medicine dropper, flow by gravity to, and remain or deposit in an effective amount at a desired area of topical application, a viscosity preferably greater than that of water was provided by including a viscosity augmenter. For compatibility with ciprofloxacin and other constituents of the preparation, preferred viscosity augmenters were non-ionic and unaffected by pH and ionic level. Aqueous solutions of ionic polymers such as carboxyvinyl polymer or polyacrylic acid, such as commercially available under the tradename Carbopol, and sodium carboxymethylcellulose were found to have undesirable viscosity variability with ionic level and pH. Other materials tried required undesirably high concentrations to produce a suitable level of viscosity. Example 1 below shows results for materials tested. All concentrations are in weight percent.

EXAMPLE 1

|  | Viscosity CTS |
| --- | --- |
| Hydroxypropylcellulose, 2% | 7.1 |
| Hydroxypropylmethylcellulose, | 13.7 |
| Cellulose gum, 0.5% | 16.3 |
| Carboxymethylcellulose, 1% | 11.2 |
| Polyvinyl alcohol, 4% | 24 |
| Polyvinylpyrrolidone, 20% | 16.7 |
| Polyvinylpyrrolidone, 30% | 63.7 |
| Methylcellulose, 0.5% | 13.3 |
| Methylcellulose, 0.65% | 49.4 |
| Carbopol, 0.02%, pH 4.7 | 18.5 |
| Carbopol, 0.036%, pH 3.9 | 4.7 |
| Carbopol, 0.036%, pH 4.75 | 203 |

Methylcellulose as commercially available under the tradename Methocel A4M from Dow Chemical Co. imparted an effective level of viscosity in low concentrations to the preparation. Amounts of methylcellulose effective to augment viscosity of aqueous solutions of ciprofloxacin hydrochloride range from about 0.1 to about 3 weight percent, preferably from about 0.1 to about 2 weight percent, and most preferably about 0.6 weight percent.

To allow the aqueous preparation to wet and spread on hydrophobic skin surface at the site of infection or inflammation in the ear canal, a surface active agent or surfactant was desirable. Non-ionic surfactants were indicated. The surfactant known as polysorbate, in particular ranging from polysorbate 20 to 80, commercially available under the tradename Tween from ICI Americas, Inc. in experimental determinations was found to provide satisfactory contact angle on hydrophobic surfaces of Teflon and clean glass. Polysorbate commercially available from other manufacturers, and in particular, conforming to USP or NF specifications is also suitable. Amounts of polysorbate ranging from polysorbate 20 to 80 effective for spreading the compositions of this invention on a hydrophobic skin surface range from about 0.01. to about 2 weight percent, preferably from about 0.05 to about 1 weight percent, and most preferably about 0.1 weight percent.

Approximate isotonicity was a desirable condition in the ciprofloxacin preparation, which was imparted by the addition of glycerin. Amounts of glycerin effective to adjust the tonicity of the composition to a level of from about 200 to about 600 milliosmoles range from about 0.1 to about 5 weight percent, preferably from about 0.1 to about 2 weight percent, and most preferably about 1 weight percent.

EXAMPLE 2

A batch of the solution composition provided by this invention was prepared by the following procedure. Glassware and passivated steel vessels and accessories free of visible iron ion residue such as rust were used exclusively. The preparation was conducted in the absence of daylight under sodium vapor lamps or yellow light. Transfers of solutions were made avoiding foaming. To 16364 grams of purified water heated to about 80 to 90 C was added with mixing 162.5 grams of methylcellulose, specifically, Methocel A4M, supplied by Dow Chemical Co. Mixing continued until the Methocel A4M was uniformly dispersed or dissolved. The solution was then cooled to about 20 to 25 C. To 500 grams of purified water was added 25 grams of Tween 20, USP/NF with mixing until dissolved. This Tween 20 solution was added to the Methocel A4M solution. Also added were 237.5 grams of glycerin, USP/NF and 63.75 grams of glacial acetic acid, USP/NF. Into 1510 grams of purified water was dissolved 170 grams of sodium acetate trihydrate, USP/NF and subsequently 335 grams of potassium sorbate, USP/NF. This solution was added to the Methocel A4M-Tween 20 solution. To the combined solutions was added 58.3 grams of ciprofloxacin hydrochloride as commercially available from Bayer A G of a purity corresponding to USP/NF. Sufficient water was added to bring the combined solution to 24500 ml, and then the pH was adjusted to a range of about 4.5 to about 5.0, preferably to about 4.75, with 1N hydrochloric acid or 1N sodium hydroxide. The total volume was brought up to 25000 ml with purified water and filtered. Portions of the solution were stored in 10 ml type 1 flint glass bottles at 50 C for three months without discoloration or other indication of instability. The composition of this batch is set out in Table 1 following.

TABLE 1

| Ingredient | Concentration Weight % |
| --- | --- |
| Ciprofloxacin hydrochloride | 0.2332 |
| Polysorbate 20 | 0.10 |
| Methylcellulose | 0.65 |
| Potassium sorbate | 0.134 |
| Sodium acetate | 0.41 |
| Acetic acid | 0.7 |
| Glycerin | 0.95 |
| Sodium hydroxide, 1N | as required |
| Hydrochloric acid, 1N | as required |
| Water | 96.8228 |

Other batches of solution with and without ciprofloxacin were prepared by the described procedure. Specimens of solutions with and without ciprofloxacin were shown to be non-ototoxic in guinea pig models.

EXAMPLE 3

Four groups, each consisting of a minimum of 5 male and 5 female NIH pigmented guinea pigs, received 10 μl of either: a solution of composition according to Table 1; a solution of composition according to Table 1 without ciprofloxacin; 0.9% sodium chloride; or 10% neomycin sulfate by direct: application to the niche of the round window membrane via implanted cannula twice a day for 30 consecutive days. Hearing assessments were performed by auditory brain-stem response once pretreatment (baseline) and on days 14 and 30. Bodyweights were monitored on days 0, 14, and 30, and the animals were observed daily for clinical signs of systemic toxicity. At termination on day 30, the middle ear was examined grossly and the cochlea was removed for inner ear histologic evaluation. The hair cells in each cochlea were assessed using a photomicroscope under epiflourescent illumination, and counted to yield a cytocochleogram.

In each of the first three groups, a few animals exhibited a minor hearing loss (20–30 dB). However, these animals did not have an increased loss of inner ear cochlear hair cells. The hearing loss was considered to be of middle ear origin, associated with the fibrous tissue around the cannula implanted in the middle ear, and, thus not related to the administration of the test materials. In the fourth group, the 10% neomycin positive control caused a major functional hearing loss and a massive structural loss of inner and outer cochlear hair cells.

The other animals did not exhibit any appreciable hearing loss. The results of this study demonstrated that neither the solution of composition according to Table 1, with or without ciprofloxacin, nor saline, cause structural or functional ototoxicity. The dose volume used was approximately 50 times the volume anticipated to be present at the round window membrane in human treatment.

Another embodiment of the invention provides a non-ototoxic, non-irritating and non-sensitizing ciprofloxacin-containing otic composition suitable for the inclusion of the anti-inflammatory glucocorticoid agent hydrocortisone. Water, being not ototoxic, irritating or sensitizing in the ear, was employed as the composition base. Amounts of ciprofloxacin hydrochloride in aqueous solution effective for anti-bacterial action range from about 0.01 to about 1 weight percent, preferably from about 0.1 to about 0.5 weight percent, and most preferably about 0.2 weight percent. Amounts of hydrocortisone effective for anti-inflammatory action range from about 0.1 to about 3 weight percent, preferably from about 0.1 to about 2 weight percent, and most preferably about 1 weight percent.

The inclusion of hydrocortisone because of its very low solubility in water required development of an aqueous suspension of hydrocortisone with ciprofloxacin hydrochloride. A pharmaceutical composition desirably has a reasonable shelf life, preferably two years, for the convenience of the user. Thus any insoluble constituents should tend to remain in suspension, or be readily resuspended by moderate shaking of the container. Uniformity of dispersion and a high degree of dispersion throughout the composition in the container allow a uniform and repeatable dose to be withdrawn for delivery to the host.

Since redispersibility is one of the major considerations in assessing the acceptability of a suspension, and since the sediment formed should be easily dispersed by moderate shaking to yield a homogeneous systems measurement of the sedimentation volume and its ease of redispersion form two of the most common basic evaluative procedures according to the *Theory and Practice of Industrial Pharmacy* by L. Lochman, H. A. Lieberman, J. L. Kanig, 2nd Edition, pages 159, 180. The methods suggested in this text were adapted to assess resuspendability and sedimentation rate of candidate compositions and to discover materials enhancing the suspension of hydrocortisone in an aqueous base. Resuspendability of candidate constituents and compositions was assessed by the number of inversions, termed strokes, required to redisperse sedimentation which was visible in a bottle containing specimens of composition after standing undisturbed overnight. Sedimentation rate was assessed by observing the height in millimeters of the column of sedimentation visible in 20 milliliters of specimen suspension contained in a cylinder after shaking and then standing undisturbed overnight. Larger heights were favorable indicating less separation with less supernatant liquid and less compaction of sedimentation.

To allow a ciprofloxacin preparation to be administered in drops from a medicine dropper, flow by gravity to and remain or deposit in an effective amount at a selected area for topical application, a viscosity augmenting agent which would also serve to suspend hydrocortisone was desirable. A large number of agents were evaluated by the above procedure for their ability to suspend hydrocortisone in an aqueous solution of ciprofloxacin hydrochloride and augment viscosity of the composition to a viscosity greater than that of water. For compatibility with ciprofloxacin hydrochloride solubility, such agents were preferably non-ionic and unaffected by pH and ionic level. Aqueous solutions of ionic polymers such as Carbopol and sodiumcarboxymethylcellulose were found to have undesirable viscosity variability with ionic level and pH. Other materials tried required undesirably high concentrations to produce a suitable level of viscosity. Methylcellulose imparted an effective level of viscosity in low concentrations to the preparation, but was found ineffective in suspending hydrocortisone.

Polyvinyl alcohol in concentrations of about 2 weight percent produced a suitable viscosity and displayed a high ability to suspend hydrocortisone in aqueous preparations in tests performed as described above and shown in the following example employing 99% hydrolyzed polyvinyl alcohol.

EXAMPLE 4

| | |
|---|---|
| Strokes to redisperse after standing overnight | 4 |
| Specimen ht, original, mm | 50 |
| Sedimentation ht after standing overnight, mm | 9 |

In comparisons with compositions with fully dissolved polyvinyl alcohol, compositions with partially dissolved polyvinyl alcohol showed fewer strokes and larger sedimentation volume. However, because of anticipated variability and change in the amount dissolved over varying temperature conditions expected to occur in storage, compositions with fully dissolved polyvinyl alcohol were preferred. Polyvinyl alcohol in an 85% hydrolyzed grade was effective in suspending hydrocortisone. However, polyvinyl alcohol in a medium viscosity grade, 99% hydrolyzed, was determined to be superior in suspending hydrocortisone. Such material is commercially available under the tradename Airvol 125 from Air Products and Chemicals Inc. Amounts of polyvinyl alcohol effective to augment the viscosity of and to suspend hydrocortisone in aqueous compositions with ciprofloxacin hydrochloride range from about 0.1 to about 10 weight percent, preferably from about 1 to about 5 weight percent, and most preferably about 2 weight percent.

The addition of lecithin in a concentration of about 0.15 weight percent enhanced the efficacy of polyvinyl alcohol in suspending hydrocortisone in aqueous preparations with ciprofloxacin hydrochloride and other components. Two grades were evaluated in suspendability trials A fully hydrogenated soy lecithin comprising 90% phosphatidylcholine commercially available under the tradename Phospholipon 90H from American Lecithin Co. was efficacious. A soy lecithin comprising 75% phosphatidylcholine commercially available under the tradename Lipoid-S75 from Vernon Walden, Inc. also was efficacious. Amounts of lecithin effective to augment the suspension of hydrocortisone in aqueous compositions with ciprofloxacin hydrochloride and polyvinyl alcohol range from about 0.01 to about 5 weight percent, preferably from about 0.01 to about 2 weight percent, and most preferably about 0.15 weight percent.

To prevent contamination by microorganisms and provide a reasonable shelf life, inclusion of a preservative in the otic pharmaceutical preparation was desirable. The required properties for a preservative compatible with ciprofloxacin were met with difficulty. Acceptable preservatives were required to cause no or little ototoxicity, sensitization or irritation of the ear canal or middle ear. Another requirement was that the preservative be jointly soluble with ciprofloxacin in water over a common pH range inasmuch as ciprofloxacin solubility was determined to be limited to a narrow pH range. In aqueous solutions containing from about 0.2 to about 1 weight percent of ciprofloxacin hydrochloride, crystalline precipitation was observed to occur at pH is above 5.5 at room temperature, and at pH's above 5 at 5 C.

In suspendabilty trials, benzyl alcohol at concentrations of about 0.9 weight percent enhanced or did not impair the suspendability of hydrocortisone in the preparation. In preservative challenge tests conducted pursuant to the procedure described in the United States Pharmacopeia, Edition XXIII, 1995, page 1681, hereby incorporated by reference, benzyl alcohol was determined to be effective as a preservative at concentrations of 0.9, 0.72 and 0.45 weight percent in aqueous ciprofloxacin hydrochloride preparations. Amounts of benzyl alcohol effective as a preservative in aqueous preparations with ciprofloxacin hydrochloride range from about 0.1 to about 3 weight percent, preferably from about 0.1 to about 2 weight percent, and most preferably about 0.9 weight percent. The solubility of ciprofloxacin hydrochloride being unaffected by benzyl alcohol, solutions of these materials may have a pH below about 6, and preferably about 4.75.

Inclusion of a buffering agent, although not necessary, was preferred. Acetate buffer was found effective at a concentration of 0.05 molar. The acetate buffer was also determined to enhance or not impair the suspendability of hydrocortisone in the preparation. Amounts of sodium acetate and acetic acid effective to buffer the preparation range from about 0.1 to about 3 weight percent of sodium acetate and from about 0.01 to about 10 weight percent of acetic acid; preferably from about 0.1 to about 2 weight percent of sodium acetate and from about 0.1 to about 5 weight percent of acetic acid; and most preferably about 0.4 weight percent of sodium acetate and about 0.7 weight percent of acetic acid.

To allow the aqueous preparation to wet and spread on hydrophobic skin surface at the site of infection or inflammation in the ear canal, a surface active agent or surfactant was desirable. Non-ionic surfactants were indicated. The surfactant known as polysorbate, in particular ranging from polysorbate 20 to 80, commercially available under the tradename Tween from ICI Americas, Inc. in experimental determinations was found to provide satisfactory contact angle on hydrophobic surfaces of Teflon and clean glass. Polysorbate commercially available from other manufacturers, and in particular, conforming to USP or NF specifications is also suitable. Tween 20 and Tween 80, in concentration of 0.1 weight percent, were determined to be effective in enhancing or not impairing the suspendability of hydrocortisone in an aqueous preparation with ciprofloxacin hydrochloride and polyvinyl alcohol. Amounts of polysorbate ranging from polysorbate 20 to 80 effective for spreading the compositions of this invention on a hydrophobic skin surface range from about 0.01 to about 2 weight percent, preferably from about 0.05 to about 1 weight percent, and most preferably about 1 weight percent.

Approximate isotonicity was a desirable condition in the ciprofloxacin preparation, which was imparted by the addition of sodium chloride. Sodium chloride in concentrations of about 0.9 weight percent were determined to be effective in enhancing or not impairing the suspendability of hydrocortisone in an aqueous preparation with ciprofloxacin and other constituents. Amounts of sodium chloride effective to adjust the tonicity of the composition from about 200 to about 600 milliosmoles range from about 0.1 to about 5 weight percent, preferably from about 0.1 to about 2 weight percent, and most preferably about 0.9 weight percent.

EXAMPLE 5

A batch of the composition provided by this invention was prepared by the following procedure. Glassware and passivated steel vessels and accessories free of visible iron ion residue such as rust were used exclusively. The preparation was conducted in the absence of daylight under sodium vapor lamps or yellow light. Transfers of solutions were made avoiding foaming. Purified water in an amount of 15255 grams was heated to 90 to 95 C and then cooled to 20 to 25 C under a nitrogen environment, and held for later use for pre-mixing, rinsing, and final volume makeup. To 15255 grams of purified water heated to about 90 to 95 C was added with mixing until fully dissolved, 500 grams of polyvinyl alcohol. To this solution was added 36.5 grams of Phospholipon 90H (lecithin) with mixing until fully dispersed. While purging nitrogen into the headspace of the container of this solution, cooling to 40 to 50 C was started. To this solution was added 25 grams of benzyl alcohol, USP/NF with mixing until dissolved. Nitrogen purging and cooling was continued to 20 to 25 C. Mixed in was 63.75 grams of glacial acetic acid, USP/NF. In a separate container, 225 grams of sodium chloride, USP/NF and 170 grams of sodium acetate trihydrate, USP/NF were dissolved in 1525 grams of purified water and then added to the main batch. Into 2743 grams of purified water in a separate container, 25 grams of polysorbate 20, USP/NF was dissolved. Added was 250 grams of hydrocortisone, micronized, USP/NF with mixing until wetted and dispersed. Added and dissolved into the main batch under nitrogen purging, was 58.3 grams of ciprofloxacin hydrochloride, of a purity corresponding to USP/NF, equivalent to 0.2 weight percent ciprofloxacin. (Alternately, ciprofloxacin hydrochloride may be predisolved in approximately 3000 grams of water along with the glacial acetic acid and sodium acetate trihydrate, and then added to the main batch.) The hydrocortisone premix was added to the main batch and mixed. Purified water was added to bring the batch to 24500 milliliters, and the pH was adjusted to 4.75 using 1N hydrochloric acid or 1N sodium hydroxide. Purified water was added to bring the batch to 25000 milliliters. The composition of this batch is set out in Table 2 following.

| Ingredient | Concentration Weight % |
| --- | --- |
| Ciprofloxacin hydrochloride | 0.2332 |
| Hydrocortisone | 1. |
| Polysorbate 20 | 0.10 |
| Polyvinyl alcohol | 2. |
| Phospholipon 90 H | 0.15 |
| Benzyl alcohol | 0.9 |
| Acetic acid | 0.7 |
| Sodium acetate | 0.41 |
| Sodium chloride | 0.9 |
| Sodium hydroxide, 1N | as required |
| Hydrochloric acid, 1N | as required |
| Water | 93.6068 |

Results of the dispersibility and settling test on a specimen of the composition set out above conducted pursuant to the procedure described above gave the results shown in the example below.

EXAMPLE 6

| | |
| --- | --- |
| Strokes to redisperse after standing overnight | 3 |
| Specimen ht, original, mm | 50 |
| Sedimentation ht after standing overnight, mm | 11 |

Specimens of this batch were stored at 5 C and at 50 C for one month. Other specimens were subjected to one week of freezing and thawing cycling. No appreciable change in either the sedimentation volume or redispersibility was noted in any of these. Results of a dispersibility and settling test on a specimen of the composition set out above after storage for one month at 50 C, conducted pursuant to the procedure described above gave the results shown in example below.

EXAMPLE 7

| | |
| --- | --- |
| Strokes to redisperse after standing overnight | 3–4 |
| Specimen ht, original, mm | 50 |
| Sedimentation ht after standing overnight, mm | 9–10 |

Other batches of the composition of Table 2, with and without ciprofloxacin, were prepared by the described procedure. Specimens of such preparations with and without ciprofloxacin were shown to be non-ototoxic in guinea pig animal models.

EXAMPLE 8

Three groups, each consisting of a minimum of 5 male and 5 female NIH pigmented guinea pigs, received 10 µl of either a composition according to Table 2; a composition according to Table 2 without ciprofloxacin; or a composition according to Table 2 without ciprofloxacin and hydrocortisone, by direct application to the niche of the round window membrane via implanted cannula twice a day for 30 consecutive days. Hearing assessments were performed by auditory brain-stern response once pretreatment (baseline) and on days 14 and 30. Body weights were monitored on days 0, 4, and 30, and the animals were observed daily for clinical signs of systemic toxicity. At termination on day 30, the middle ear was examined grossly and the cochlea was removed for inner ear histologic evaluation. The hair cells in each cochlea were assessed using a photomicroscope under epifluorescent illumination, and counted to yield a cytocochleogram.

One animal in the first group and one animal in the second group exhibited a minor hearing loss (20–40 dB). However, these animals did not have an increased loss of inner ear cochlear hair cells. The hearing loss was considered to be of middle ear origin, associated with the fibrous tissue around the cannula implanted in the middle ear, and thus, not related to the administration of the test materials.

The other animals did not exhibit any appreciable hearing loss. The results of this study demonstrated that none of the compositions applied cause either structural or functional ototoxicity.

Yet another embodiment of the invention provides a non-ototoxic, non-irritating and non-sensitizing ciprofloxacin-containing otic solution composition wherein glycerine augments the viscosity of the aqueous solution to a viscosity greater than that of water. Glycerine concentrations of from about 50 to about 95 weight percent provide usable viscosities ranging from about 10 to about 200 centistokes. Preferred glycerine concentrations range from about 70 to 90 weight percent, most preferably 87 weight percent. Concentrations of ciprofloxacin in such aqueous solutions effective for anti-bacterial action range from about 0.01 to about 1 weight percent, preferably from about 0.1 to about 0.5 weight percent, most preferably about 0.2 weight percent.

A buffer may be included to provide a pH range to maintain the solubility of ciprofloxacin hydrochloride in the composition. A range of pH of from about 3 to about 6 is suitable. Amounts of sodium acetate and acetic acid effective to buffer the composition range from about 0.01 to about 2 weight percent of sodium acetate and from about 0.01 to about 5 weight percent of acetic acid; preferably from about 0.02 to about 1 weight percent of sodium acetate and from about 0.1 to about 2 weight percent of acetic acid; and most preferably about 0.05 weight percent of sodium acetate and about 0.16 weight percent of acetic acid.

EXAMPLE 9

In accordance with this embodiment, a solution was prepared having 0.2 weight percent ciprofloxacin, 87.0 weight percent glycerine, 0.05 weight percent sodium acetate, 0.16 weight percent acetic acid, the balance being water. This composition was determined to be adequately resistant to contamination by microorganisms over a reasonable shelf life. However, a preservative, such as, for instance, potassium sorbate or benzyl alcohol, may be included for added protection. In view of the tests performed on guinea pigs with other compositions including the ingredients of this solution, this solution its non-ototoxic, non-sensitizing and non-irritating applied topically to the external and middle ear in humans.

EXAMPLE 10

Clinical Study Results

The present study was undertaken to determine the efficacy and safety of a one week treatment course of CIPRO® otic drops, with or without hydrocortisone for the treatment of acute diffuse bacterial otitis externa. 493 Patients, ≧2 years of age, with acute otitis externa were enrolled in this prospective, multicenter, randomized trial comparing the safety and efficacy of ciprofloxacin otic drops (0.2%), with or without hydrocortisone, each for seven days. Patients with clinically documented otitis (i.e., edema, otalgia, and tenderness) of less than three weeks duration were considered valid for efficacy. 249 patients were evaluated for efficacy with ciprofloxacin alone [CIP Soln], and 244 patients for ciprofloxacin plus hydrocortisone [CIP/HC Susp]. Clinical resolution or improvement was observed in 93% and 90%, CIP Soln- and CIP/HC Susp-treated patients, respectively (see Table 1). At the end of treatment, CIP Soln and CIP/HC Susp were statistically equivalent. Clinical response appeared to be similar among the treatment groups regardless of age, although patients ≧17 years had complete resolution less frequently. Estimated median time to end of ear pain was 4.6 days (CIP Soln), and 3.8 days (CIP/HC Susp). CIP/HC Susp-treated patients had a significantly shorter time to end of ear pain than CIP Soln-treated patients (P=0.036). *Pseudomonas aeruginosa* was the most frequently isolated pre-therapy pathogen in both treatment groups (87%; see Table 3). Bacteriologic eradication or presumed eradication at the end of therapy was achieved in 93% and 95% of CIP Soln- and CIP/HC Susp-patients, respectively (see Table 2). All treatments were well tolerated with similar rates of drug-related adverse events, ranging from 5% to 6%. In conclusion, ciprofloxacin otic drops, with or without hydrocortisone, were effective in the treatment of otitis externa. The addition of hydrocortisone to ciprofloxacin resulted in a statistically significant reduction in the time to end of ear pain, when compared with the ciprofloxacin monotherapy product.

Study Design and Antimicrobial Therapy

This was a prospective, randomized, non-blinded, two-arm comparative trial. Patients were randomly assigned to one of two treatment groups in consecutive fashion. Ciprofloxacin otic solution (CIP Soln) as the hydrochloride monohydrate (0.2%) and ciprofloxacin otic suspension as the hydrochloride monohydrate (0.2%) plus hydrocortisone (1%) (CIP/HC Susp) was supplied by Bayer Corporation Pharmaceutical Division, West Haven, Conn. CIP Soln and CIP/HC Susp were both buffered products. Both the CIP Soln and CIP/HC Susp were administered as three drops twice daily. Each dose of study drug was to be administered in the deep portion of the ear canal for a total duration of 7 days. The use of an ear wick was permitted; the first dose of study drug was "doubled" to saturate the ear wick (6 drops for CIP Soln and CIP/HC Susp). The first dose of each study drug was administered at the investigator's clinic. Use of oral analgesics without anti-inflammatory activity for pain relief were permitted during the study period. Concomitant topical (in study ear) or systemic antibacterial or anti-inflammatory agents were not allowed for the study duration.

Antimicrobial effectiveness was evaluated by means of clinical and bacteriologic determinations, including repeat ear canal cultures. Clinical assessment included repeat ear examinations. In addition, each patient recorded the presence of ear pain two- to three-times daily until ear pain ended completely; the date and time of disappearance of ear pain was specifically recorded in the diary. A visual analogue pain scale (15 cm) was used in order to rate pain; the patient drew a line on the scale to indicate either the absence of pain to severe pain (Max M B, Laska E M, Single dose analgesic comparsion, In: *Advances in Pain Research and Therapy: The design of analgesic clinical trials.* Vol. 18 (M B Max, R Portenoy, E M Laska, eds), Ravis Press Limited, New York, 1991, pp 55–65). For children 2 to 6 years old, parents had to assist with the evaluation of degree of pain. Bacteriologic assessment included obtaining outer ear canal specimens for culture on all patients pre-therapy and, if material was available, at the end of therapy (i.e., 3 to 7 days post-therapy); several sites obtained specimens for culture at the end of therapy by moistening the swab for those with "dry" ears. Collection of specimens from the deep portion of the ear, with avoidance of contamination from the outer canal, involved the use of a Transwab ENT-charcoal system (Medical Wire, England) which consists of a single swab with aluminum wire shaft and Ames charcoal transport media. The culture specimen was transported within 24 hours to a central laboratory (SmithKline Beecham Clinical Laboratory, Van Nuys, Calif.). Quantitative identification of causative aerobic organisms was performed using standard methods (Murray P A, Baron E J, Pfaller M A, Tenover F C, Yolken R H, eds., Manual of Clinical Microbiology, Washington, D.C.: American Society for Microbiology. 1995:6) and minimum inhibitory concentration (MIC) susceptibility tests were conducted for ciprofloxacin only (National Committee for Clinical Laboratory Standards, Methods for dilution antimicrobial susceptibility tests for bacteria that grow aerobically, Document M7-A2, 2nd edition, 1990.).

Efficacy Evaluation

For a course of therapy to be considered valid for drug efficacy, the following criteria were necessarily fulfilled: (1) diagnosis of acute diffuse, bacterial external otitis established by clinical signs and symptoms including edema, otalgia, and tenderness; (2) clinical response must have been evaluated at the end of therapy; (3) study drug must have been given for 7 full days with 90% compliance, unless treatment was a failure; and (4) no other systemic antimicrobial agent could have been administered concomitantly with the study drug (from pre-therapy to the end-of-therapy evaluation) in the treatment ear.

The effectiveness of the study drug was determined on the basis of the clinical response of the patient and the presumed or documented bacteriologic response of the infecting organism. Clinical response, the primary efficacy variable, was based on serial examinations of the patient. At the end of therapy, clinical response was defined as resolution, improvement, or failure based on both clinical symptoms and signs and the investigator's clinical judgment of whether or not additional antimicrobial therapy was required. At the follow-up evaluation, the patients' clinical response was determined to be either continued resolution or relapse using similar criteria. In addition, CIP Soln and CIP/HC Susp were compared by evaluating the time to end of ear pain.

Bacteriologic response for causative organisms (i.e., pathogens) was determined at the end of therapy to be either eradication, presumed eradication (patients with clinical resolution and no material to culture), persistence or superinfection. Bacteriologic responses at the follow-up evaluation included: continued (usually presumed) eradication, relapse (original causative organism present) and reinfection (new causative organism identified). Bacteriologic response was considered indeterminate if a culture was not obtained or was performed at an inappropriate time.

Statistical Analysis

The primary objectives of this study were to demonstrate whether CIP Soln and/or CIP/HC Susp were efficacious and to compare the time-to-end of pain for CIP/HC Susp and CIP Soln. The primary measure of efficacy was the proportion of patients in each treatment group with clinical success (resolution plus improvement) at the end of therapy. The secondary measure of efficacy was bacteriologic eradication at end of therapy in those patients with an organism isolated pre-treatment.

For the end of therapy and follow-up clinical and bacteriologic responses, 95% two-sided confidence intervals (95% CI) were calculated for the differences between resolution or eradication rates; a Mantel-Haenszel weighting procedure was used to adjust for a possible center effect. Each of the two treatment comparisons were declared equivalent at the 2.5% significance level if the lower bound of the confidence interval was $\geq -0.10$. A clinical outcome evaluation as a function of patient subgroups (i.e., $\leq 12$ years and >12 years) was also conducted to further evaluate the efficacy of the study drugs. These analyses were performed for the efficacy valid population. For comparison of time-to-end of ear pain for CIP/HC Susp and CIP Soln, the log rank test was employed.

Categorical variables, including demographic and medical characteristics, were analyzed using a Cochran-Mantel-Haenszel test. For continuous variables, a two-way analysis of variance (ANOVA) model was fitted with treatment group and center as factors. The incidence rates of adverse events were tabulated by treatment group and body system.

Microbiologic Response

Of ear canal cultures from the patients evaluable for the efficacy analysis, 65% CIP Soln and 64% CIP/HC Susp patients had one or more causative organisms isolated pre-therapy. Bacteriologic eradication at the end of therapy, including presumed eradication, was 93% in the CIP Soln- and 95% in the CIP/HC Susp-treatment groups (Table 2). Bacterial colonization in the ear canal were reported for 19 patients (13 CIP Soln, 6 CIP/HC Susp). None of the patients with colonizing organisms were treated with additional antimicrobial therapy, although four patients were clinical failures (*Achromobacter* species, *P. aeruginosa* x 2, *Streptococcus* species).

TABLE 1

Clinical Response by Age Group at the End of Therapy following Ciprofloxacin and Ciprofloxacin/Hydrocortisone Therapy

| Age | Response | Ciprofloxacin Solution n (%) | Ciprofloxacin/ Hydrocortisone Suspension n (%) |
|---|---|---|---|
| 2–6 years | Resolution/Improvement | 27 (96.5) | 22 (100) |
| | Failure | 1 (3.5) | 0 (0) |
| 7–12 years | Resolution/Improvement | 64 (94) | 75 (96) |
| | Failure | 4 (6) | 3 (4) |
| 13–16 years | Resolution/Improvement | 26 (96) | 19 (90.5) |
| | Failure | 1 (4) | 2 (9.5) |
| $\geq$17 years | Resolution/Improvement | 108 (91) | 102 (85) |
| | Failure | 11 (9) | 18 (15) |

TABLE 2

Bacteriologic Response for the Efficacy Evaluable Population Following Ciprofloxacin and Ciprofloxacin/Hydrocortisone Therapy

| Time of Evaluation | Response | Ciprofloxacin Solution n (%) | Ciprofloxacin/ Hydrocortisone Suspension n (%) |
|---|---|---|---|
| End of Therapy | Eradication/Presumed Erad | 142 (93) | 139 (95) |
| | Superinfection | 8 (5) | 4 (3) |
| | Persistence | 3 (2) | 3 (2) |
| 14–28 day Follow-up | Continued Eradication | 44 (94) | 52 (95) |
| | Relapse | 1 (2) | 2 (3) |
| | Reinfection | 2 (4) | 1 (2) |

TABLE 3

Bacteriologic Eradication by Organism At the End of Ciprofloxacin or Ciprofloxacin/Hydrocortisone Therapy

| Organism | Ciprofloxacin Solution n (%)† | Ciprofloxacin/Hydrocortisone Suspension n (%) |
|---|---|---|
| *P. aeruginosa* | 143 (99) | 132 (99) |
| Pseudomonas species | 6 (100) | 2 (100) |
| *S. amltophilia* | 6 (86) | 5 (100) |
| Enterobacter species | 8 (100) | 8 (100) |
| Acinetobacter species | 7 (100) | 10 (100) |
| Klebsiella species | 4 (100) | 9 (100) |
| Miscellaneous gram negative bacilli/cocci* | 23 (100) | 16 (100) |
| *S. aureus* | 13 (100) | 16 (94) |
| Streptococcal species | 2 (100) | 1 (100) |
| Total | 212 (99) | 199 (99) |

† number organisms eradicated plus presumed eradicated.
*Miscellaneous = *Proteus mirabilis* (n = 4), Serratia species (n = 2), *Escherichia coli* (n = 2), Citrobacter species (n = 6), Flavimonas species (n = 1), Aeromonas species (n = 3), Achromobacter species (n = 2), Providencia species (n = 1), Alcaligenes species (n = 2) (ciprofloxacin); Citrobacter species (n = 1), *E. coli* (n = 3), *Proteus mirabilis* (n = 6), Serratia species (n = 3), Flavimonas species (n = 1), Chryseomonas species (n = 1), Weeksella zoohelcum (n = 1) (ciprofloxacin/hydrocortisone); *Proteus mirabilis* (n = 4), Serratia species (n = 5), *E. coli* (n = 2), Citrobacter species (n = 1), Flavimonas species (n = 1), Chryseomonas species (n = 2), Achromobacter species (n = 1) (PNH).

The foregoing embodiments and examples are to be considered illustrative, rather than restrictive of the invention, and those modifications which come within the meaning and range of equivalence of the claims are to be included therein.

What is claimed is:

1. A method of treating otitis which comprises introducing an antibacterially-effective amount of a composition comprising a non-ototoxic, topical, otic pharmaceutic composition comprising:
(a) ciprofloxacin in aqueous solution in an amount effective for antibacterial action;
(b) a non-ionic viscosity augmenter unaffected by pH and ionic level, said viscosity augmenter being present in an amount effective for augmenting viscosity of the composition to a viscosity greater than that of water, said viscosity augmenter being at least 85% hydrolyzed polyvinyl alcohol;
(c) a non-ototoxic preservative present in an amount effective for antibacterial action, said preservative being benzyl alcohol;
(d) water sufficient to produce an aqueous composition;
(e) hydrocortisone in aqueous suspension in an amount effective for anti-inflammatory action;
(f) lecithin in an amount effective for enhancing suspension of other constituents in the composition; and
(g) polysorbate ranging from polysorbate 20 to 80 in an amount effective for spreading the preparation on a hydrophobic skin surface to the site of infection or inflammation.

* * * * *